(12) United States Patent
Falconer et al.

(10) Patent No.: US 7,306,581 B2
(45) Date of Patent: Dec. 11, 2007

(54) POUCH FOR COLLECTING HUMAN WASTE

(75) Inventors: Malcolm Falconer, London (GB); Adrian Breakwell, Chester (GB); Bret Weig, Browns Mills, NJ (US)

(73) Assignee: Bristol-Myers Squibb Company, New York, NY (US)

( * ) Notice: Subject to any disclaimer, the term of this patent is extended or adjusted under 35 U.S.C. 154(b) by 385 days.

(21) Appl. No.: 10/607,343

(22) Filed: Jun. 26, 2003

(65) Prior Publication Data

US 2004/0049837 A1    Mar. 18, 2004

(30) Foreign Application Priority Data

Jul. 4, 2002    (GB)    ................ 0215381.5

(51) Int. Cl.
*A61F 5/44* (2006.01)
(52) U.S. Cl. ............. 604/332; 604/337; 604/339; 604/343; 604/344
(58) Field of Classification Search ............. 604/332, 604/337, 339, 343, 344
See application file for complete search history.

(56) References Cited

U.S. PATENT DOCUMENTS

| | | | | |
|---|---|---|---|---|
| 4,755,177 A | * | 7/1988 | Hill | .............. 604/336 |
| 5,968,023 A | * | 10/1999 | Olsen | ............. 604/334 |
| 6,336,918 B1 | | 1/2002 | Olsen et al. | |
| 6,887,222 B2 | * | 5/2005 | Mandzij et al. | ............ 604/332 |
| 2003/0028160 A1 | | 2/2003 | Leise, Jr. et al. | |

FOREIGN PATENT DOCUMENTS

| | | |
|---|---|---|
| EP | 1197193 A3 | 10/2003 |
| GB | 1447314 | 8/1976 |
| WO | WO 03/065944 A1 | 8/2003 |
| WO | WO 03/086250 A1 | 10/2003 |

* cited by examiner

*Primary Examiner*—Jacqueline F. Stephens
(74) *Attorney, Agent, or Firm*—Stuart E. Krieger

(57) ABSTRACT

A drainable ostomy pouch has an outlet. Reinforcing members at the outlet are deformable by application of manual pressure at their ends to distend the outlet. The lateral edges of the reinforcing members may be offset, which encourages the reinforcing members to consistently bend away from each other. A peelable distributed mechanical engagement fastener secures the outlet in a folded condition. The fastener parts are hook-hook type plastic extrusions, and provide a snap-engagement. A security flap is foldable under the outlet when in its folded condition. The outlet is released in two stages.

24 Claims, 17 Drawing Sheets

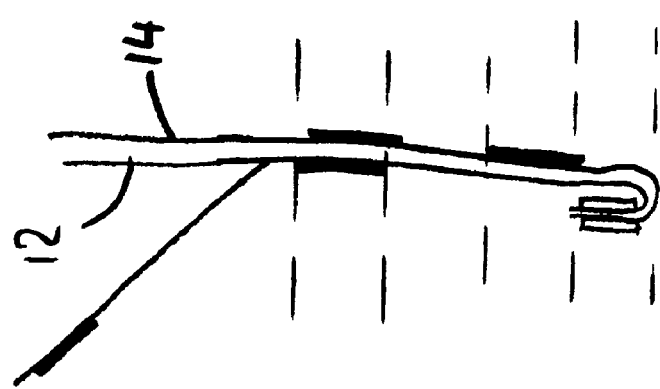
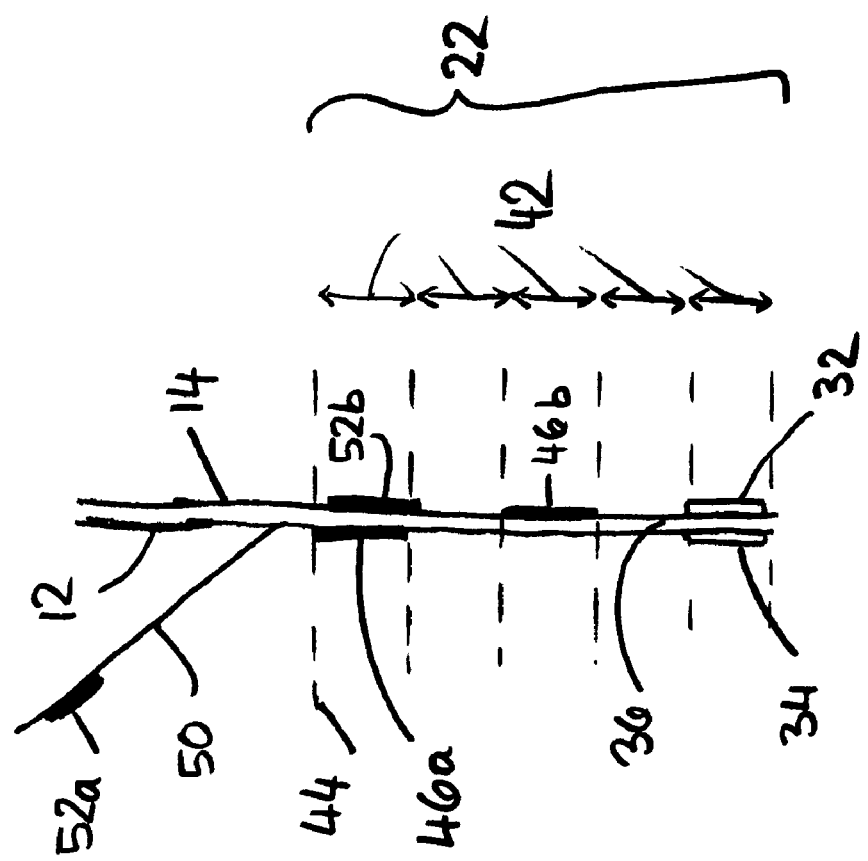
FIG. 9 (a)
FIG. 9 (b)

POUCH FOR COLLECTING HUMAN WASTE

FIELD OF THE INVENTION

The present invention relates to a pouch for collecting human waste. One example is an ostomy pouch, although other examples include incontinence and hygiene pouches, for example, urine bags. The term ostomy includes colostomy, ileostomy and urostomy. In particular, the invention relates to such a pouch which is drainable.

BACKGROUND TO THE INVENTION

Drainable pouches include an outlet through which the pouch contents may be drained to enable the pouch to be reused.

One non-limiting aspect of the invention may relate to an arrangement of one or more reinforcing members for controlling the cross-sectional shape of the outlet. The reinforcing members may be arranged to hold the outlet generally closed or constricted but, by manually squeezing the opposite edges of the outlet, the reinforcing members can be deformed to distend the opening. Such an arrangement is described, for example, in GB 2346328, U.S. Pat. Nos. 3,825,005, 2,875,451, 5,745,926 and 3,724,461.

In GB 2346328, the reinforcing members are directly opposed and together extend only partway across the drain passage in the outlet, leaving the edge portions of the drain passage without any reinforcement. The reinforcing members are creased near their midpoints, to encourage the members to bend in opposite directions when the outlet is squeezed by its edges. The creases are essential to ensure that the reinforcing members do not accidentally bend in the same direction, which is particularly a problem if the outlet surfaces are subjected to sticky faecal matter, which may tend to cause the surfaces to stick together. However, the creases inhibit the reinforcing members from sealing the outlet. The discontinuities created by the creases would result in leakage in the region of the creases.

Another non-limiting aspect of the invention may relate generally to a fastening system for fastening the outlet in a closed condition. Generally such fastening systems include either a separate fastener, for example a closure clip, which is removably fitted to the pouch outlet when it is desired to seal the outlet closed, or an integral fastener carried permanently on the pouch. This aspect of the invention may relate to an integral fastener.

A typical integral fastener for pouches is a distributed mechanical engagement fastener, for example a hook and loop type fastener in which at least one of the fastener parts is fabric-based. Pouches with such fastening systems are described, for example, in GB-A-2000683 and GB-A-2268065. A distributed mechanical engagement fastener is currently preferred instead of an adhesive fastening system because re-fastenable adhesives do not seem to provide the user with the same degree of confidence and security when used repeatedly, or for an extended period of time, or when subjected to washing. An adhesive fastener has the further disadvantage that it is difficult to clean if the adhesive is becomes soiled, and the exposed adhesive surface prevents manual "milking" of the pouch during draining.

However, fabric-based hook and loop fasteners still have drawbacks, because the fabric soils easily when contacted by human waste. The fabric also tends to absorb liquids, which makes the fastener part difficult to wipe clean, for example with a wet cloth. It is desirable for a user to be able to clean the outlet and the fastener parts by immersing the outlet in water, for example, in a sink. A fabric fastener part has the further disadvantage that the fabric is difficult to dry once it has become wet.

SUMMARY OF THE INVENTION

In a first aspect, the invention may include an outlet with first and second reinforcing members near or at the outlet. The reinforcing members may be arranged such that by squeezing the outlet at its edges, the reinforcing members may be deformed to distend the outlet.

At least one of the reinforcing members may be offset laterally relative to a centreline or axis of the outlet.

The reinforcing members may be offset laterally relative to each other.

An edge of the first reinforcing member may be offset laterally with respect to a corresponding edge of the second reinforcing member.

The above arrangements have been found surprisingly to promote bending of the reinforcing members in opposite directions when external pressure is applied to distend the outlet. This can avoid the need to provide directional creases in each of the reinforcing members to promote bending in opposite directions. Manufacturing of the pouch may be simplified, and the reinforcing members may be used to provide a primary seal when the outlet is placed in its closed condition.

The amount of the offset may be at least, or about equal to, or less than any of: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm.

The aforementioned edges may be respective edges of the reinforcing members against which external pressure may be applied in use to deform the reinforcing members to distend the opening.

At least one of the reinforcing members may overlap and extend beyond the edge of the other reinforcing member.

The reinforcing members may be of the same length and be offset in a lateral direction so as to partly overlap each other. Alternatively, the reinforcing members may be of different lengths.

At least one edge of at least one of the reinforcing members may be offset relative to an adjacent edge of the pouch material at the outlet, to provide a cushion of pouch material laterally beyond the edge of the reinforcing member. The offset relative to the edge of the pouch material may be referred to as a cushion offset. The amount of the cushion offset may be at least, or about equal to, or not greater than any of: 1 mm, or 2 mm, or 3 mm, or 4 mm, or 5 mm, or 6 mm, or 7 mm, or 8 mm, or 9 mm, or 10 mm, or 11 mm, or 12 mm, or 13 mm, or 14 mm, or 15 mm. Both edges of at least one of the reinforcing members may be offset relative to the opposite edges of the outlet to provide lateral cushions of pouch material beyond the two edges. The amounts of cushion offset may different for each edge, or they may be the same. Each cushion offset may be within the above ranges. Alternatively, one or both edges of at least one reinforcing member may be flush with an edge of the outlet.

At least one reinforcing member, or the combination of the reinforcing members together, may extend transversely across the entire width of a passage in the outlet. This may provide a continuous surface useful for forming a seal in the outlet when closed.

The reinforcing members may be of the same material, or they may be of different materials, for example, of different resilience and/or stiffness.

Preferably both corresponding lateral edges of the reinforcing members are offset laterally from each other.

The reinforcing members may be arranged to provide different magnitude radii of curvature to respective surfaces of the outlet when the reinforcing members are deformed to distend the outlet.

Such different radii of curvature may also provide advantages in promoting separation of the surfaces at the outlet, and promoting bending of the reinforcing members in different directions.

The reinforcing members may be of different lengths to provide the different radii of curvature.

The reinforcing members may be arranged such that, in use, the lateral edges of the first reinforcing member are exposed to external pressure to partly deform the first reinforcing member before the external pressure is applied to the second reinforcing member.

The reinforcing members may be of substantially the same thickness or of different thicknesses. Different thicknesses may be used to provide a different bending characteristic for each reinforcing member.

At least one of the reinforcing members may be generally planar in its relaxed or normal configuration. Additionally or alternatively, at least one of the reinforcing members may have an at least partly non-planar shape that may tend to hold the mouth at least partly open. For example, the reinforcing member may be bowed, or curved, or bent. Such a natural non-planarity may be smaller than the degree of non-planarity that may be created by squeezing the reinforcing members to distend the opening. A small natural curvature may result, for example, merely from the storage of the reinforcing members as roll stock prior to assembly of the pouch.

The reinforcing members may provide a folding guide or "mandrel" about which the outlet may be folded, in use. This may ensure consistent folding and positioning of the outlet, so that fastener parts for securing the outlet in a folded, or stowed, condition are correctly aligned.

In another aspect aspect, the invention provides a distributed mechanical fastening system for use in fastening the outlet in a closed condition. The distributed mechanical fastening system may include first and second mateable fastener parts for producing interlocking mechanical engagement distributed over a fastener area.

The first and second mateable fastener parts may both be plastics extrusions. In contrast to fabric, plastics extrusions do not soil so easily, and are considerably easier to clean and to dry.

The first and second mateable fasteners may form part of a hook-hook fastener system. The term "hook-hook" includes at least any fastener system comprising interengageable undercut projections which mate when the two fastener parts are pressed together. In contrast to hook and loop fasteners, a hook-hook fastener may have less springback, leading to closer face-to face engagement being maintained between the fastener surfaces.

The first and second fastener parts may have substantially the same fastener projections. Such fastener parts can simplify the manufacturing process for the pouch considerably, can also facilitate greater freedom of design for pouch designers, and can reduce the count of different parts and/or materials in the pouch, leading to reduced production costs.

The first and second fastener parts may provide a snap-engagement when pressed together. Such a snap-engagement may provide the user with a positive assurance that the fastener parts are firmly fastened to each other. This is extremely advantageous for users who may have reduced or impaired sight, for example as a result of old age, and who might otherwise find it difficult to assure themselves that the fastener parts are firmly engaged.

In another aspect, the invention provides an outlet for a pouch, the outlet being configured to be closed by rolling or folding the outlet from its free end towards the body of the pouch. At least one reinforcing member may be provided as aforesaid and/or extending laterally beyond at least one boundary of the drain passage at least at a position in register with the reinforcing member. The outlet may include a lateral step in its profile between the reinforcing member and a proximal end of the outlet. The lateral step may be external in the profile of the outlet, or it may be internal in the profile of the drain passage within the outlet. In addition to, or as an alternative to, a lateral step, the outlet may taper in width over at least a portion of the length of the outlet. The taper may be a gradual taper along a majority of the length of the outlet.

With such an arrangement, when the outlet is rolled or folded to its closed condition, portions of the outlet between the proximal end of the outlet and the lateral step/narrow end of the taper, may provide a cushion of material laterally outside an edge of the reinforcing member. This can improve the comfort of the user when wearing the pouch by avoiding the edge of the reinforcing member from being exposed.

Preferably, the size of the step/lateral degree of the taper in at least one edge is at least 1 mm, more preferably at least 2 mm, more preferably at least 3 mm, more preferably at least 4 mm, more preferably at least 5 mm.

Preferably, such a lateral profile step or taper is provided in both lateral edge regions of the outlet.

In another aspect, the invention provides an outlet for a pouch, the outlet being configured to be closed by rolling or folding the outlet from its free end towards the body of the pouch. An outlet fastener system may be provided for securing the outlet in its closed condition. A security flap may be folded at least partly over, or at least partly around, a portion of the outlet when the outlet is in its closed condition. A flap fastener system may be provided for fastening the security flap in its folded condition.

The flap may act as a protective, secondary fastener for maintaining the outlet in its closed condition should the main outlet fastener fail or become unfastened accidentally. The flap also provides the user with an extra degree of security and confidence against accidental opening of the outlet, which may be significant for customer acceptance. In a particularly preferred form, the security flap is configured to be folded to extend from one face of the pouch, under the folded outlet, to the other face of the pouch, thereby providing a sling under the folded outlet. This can provide an extra degree of security to assure the wearer than the outlet cannot become accidentally unfastened and drop down while the security flap is secured in position.

In a preferred form, the outlet includes a two-stage fastening arrangement which has to be unfastened in two distinct stages. A two-stage fastening arrangement may provide more control of the outflow or drainage of the pouch contents. Firstly, the user has to unfasten the flap fastener to release the security flap from around the folded outlet. Even with the security flap released, the outlet is held in its closed condition by the outlet fastener. Secondly, the user has to unfasten the outlet fastener to allow the outlet to be unfolded from its closed condition to an open condition.

The above aspects may be used independently, or yet further advantages may be obtained by using two or more of the above aspects in combination.

Although certain selected features, objects and advantages have been highlighted above, the invention is not limited to these selections. Further features, objects and advantages of the invention will become apparent from the following disclosure of preferred embodiments. The Applicant claims protection for any novel feature or combination of features described herein and/or illustrated in the drawings, whether or not emphasis has been placed thereon.

BRIEF DESCRIPTION OF THE DRAWINGS

Preferred, non-limiting embodiments of the invention are now described by way of example only, with reference to the accompanying drawings, in which:

FIGS. 9(a) to (f) are schematic side views showing the sequence of stages for folding and fastening the outlet in a closed condition;

DESCRIPTION OF PREFERRED EMBODIMENTS

Figure 1:
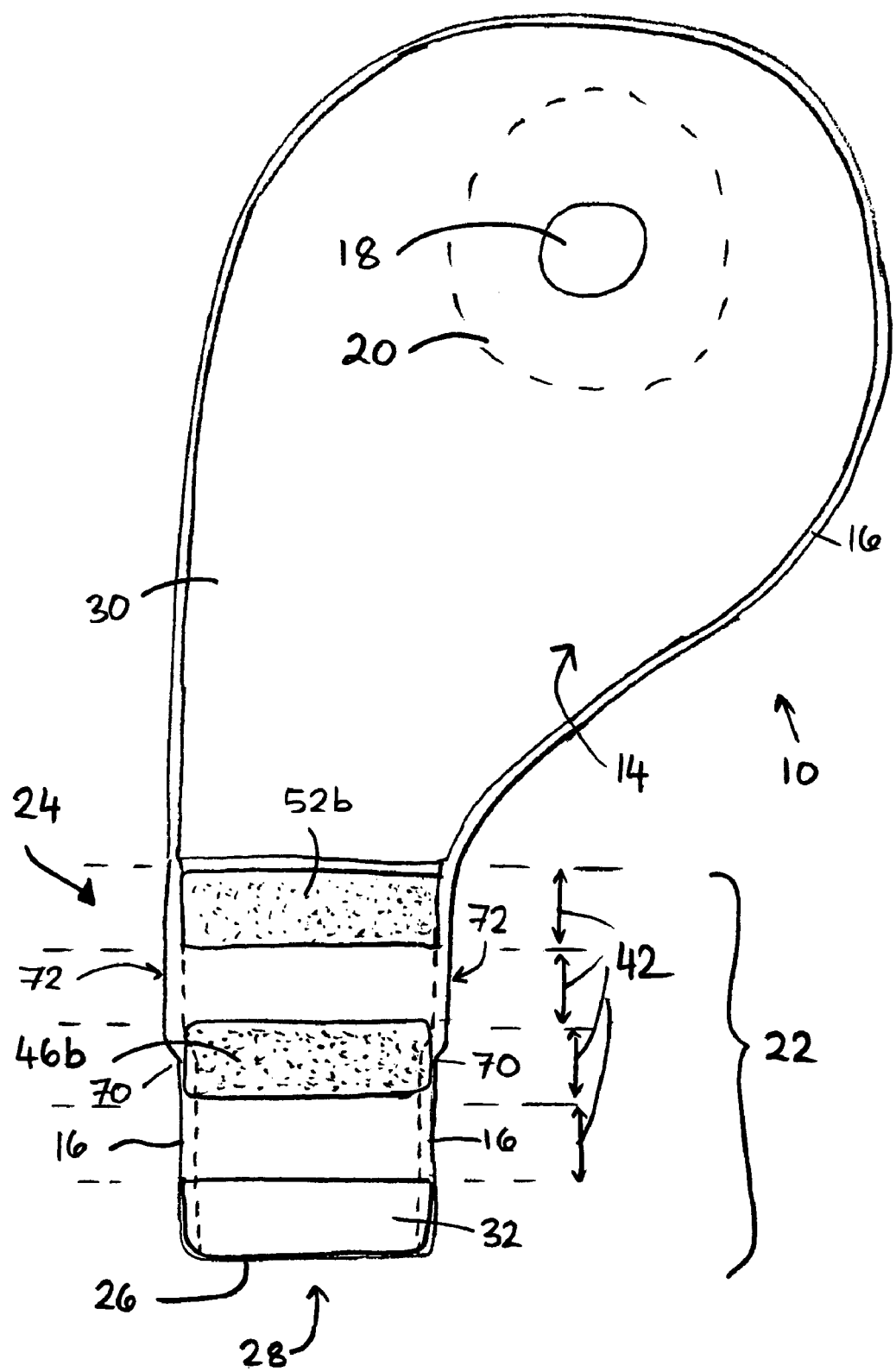
FIG. 1 is a schematic rear view of a first embodiment of drainable pouch.
Figure 2:
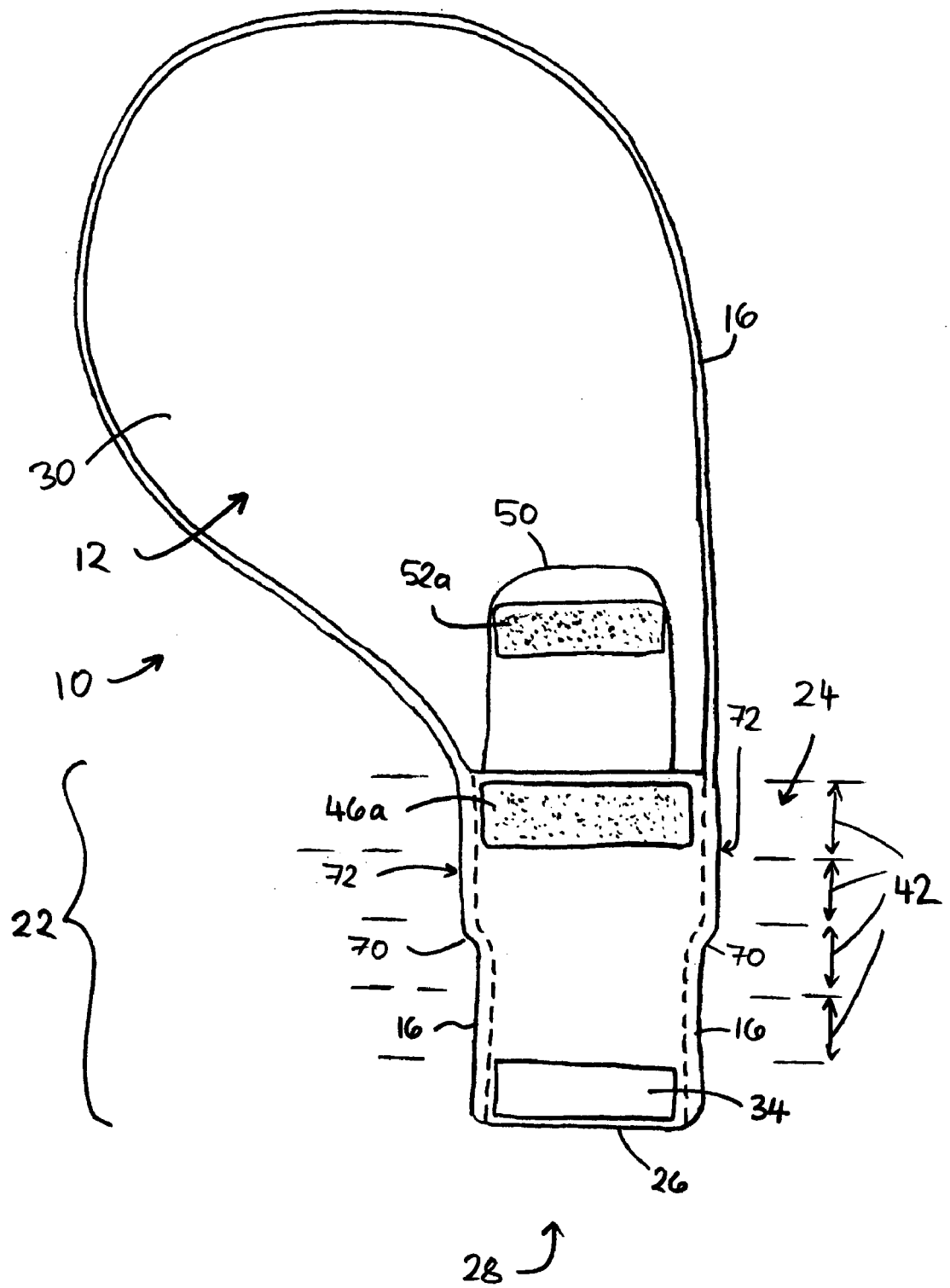
FIG. 2 is a schematic front view of the first embodiment.
Figure 3:
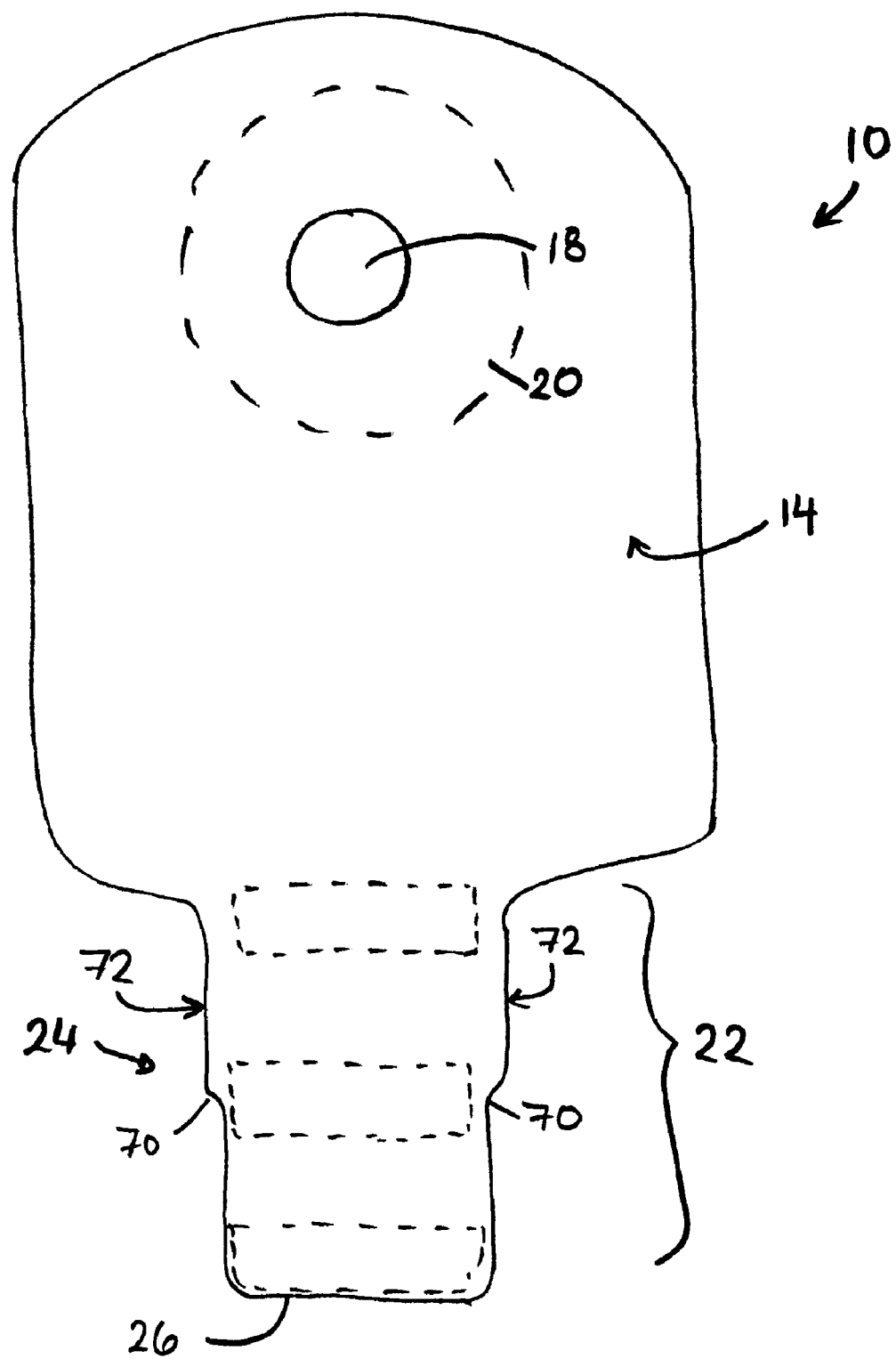
FIG. 3 is a schematic illustration of an alternative shape of ostomy pouch.

Referring to FIGS. 1 and 2, a drainable ostomy pouch 10 is formed generally by a front wall 12 and a rear wall 14 of flexible impermeable plastics film, welded together around a common periphery 16. Many suitable materials for the walls 12 and 14 are known in the art. For example, the material may be a laminate of one or more layers of ethylene vinyl acetate (EVA) and a barrier layer, for example of poly vinylidene chloride (PVDC).

The rear wall 14 of the pouch (FIG. 1) has an entrance aperture 18 in its upper region for receiving human waste from a wearer's stoma. In the illustrated embodiment, the pouch may be intended (although not exclusively) as an ileostomy pouch for receiving semi-solid ileal fluid from a wearer's ileal stoma. The pouch 10 is securable to the peristomal area of the wearer's body by a body fitment, indicated generally at 20, and including a wafer or pad of hypoallergenic skin adhesive (not shown). The pouch 10 may be of a so-called "one-piece" type in which the body fitment 20 is permanently secured to the rear wall 14 of the pouch 10 around the entrance aperture 18. Alternatively, the pouch 10 may be of a so-called "two-piece" type in which the pouch 10 and the body fitment 20 are separate items, and are removably attachable to each other, for example by a conventional adhesive coupling or by a conventional mechanical coupling.

As is conventional, the pouch 10 may include one or more internal compartments (not shown) for accommodating the human waste collected in the pouch 10. The pouch 10 may also include a conventional deodorising filter (not shown) for venting and deodorising flatus from the interior of the pouch 10.

The pouch 10 includes an outlet 22 in the form of tail portion 24 of the pouch. The term outlet may be used herein to refer to the tail portion generally. The tail portion 24 is narrower than the upper portion of the pouch 10, and has an opening 26 at its distal end 28. As can be seen in FIGS. 1 and 2, the outlet 22 may be generally asymmetrical with respect to the entrance aperture 18. This can provide an ergonomic shape of pouch 10 which is well suited to the shape and contours of a wearer. However, in alternative embodiments the outlet 22 may be generally symmetrical with respect to the entrance aperture 18 as illustrated, for example, in profile in FIGS. 3 and 16-19.

Referring again to FIGS. 1 and 2, an exterior face of one of both of the front and rear walls 12 and 14 may be at least party covered by a comfort layer 30 of a soft cushioning material. The comfort layer 30 may end at a location just above the outlet 22, so as to avoid the comfort layer 30 from interfering with fasteners for closing the outlet 22, as described further below. It is also desirable not to provide the comfort layer 30 in the region of the opening 26 at the distal end 28 of the outlet 22, as the comfort layer 30 may be of a material that soils easily, or is difficult to wipe clean.

Figure 4:
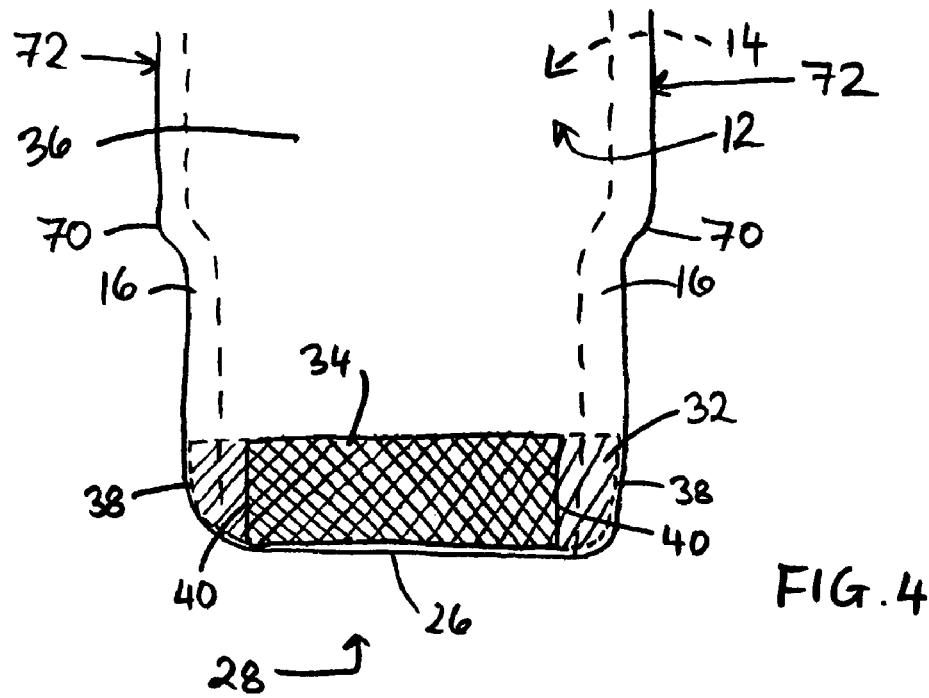
FIG. 4 is a schematic view showing a detail of the outlet of FIG. 1 in its unfolded condition.

Referring to FIG. 4, a first reinforcing member 32 is attached to the rear wall 14 of the pouch 10 at a position near, or adjacent to, the opening 26 at the distal end 28. A second reinforcing member 34 is attached to the front wall 12 of the pouch 10. The reinforcing members 32 and 34 may be attached along their lengths to the walls 14 and 12. In the illustrated embodiment, the second reinforcing member 34 generally opposes the first reinforcing member 32, although in other embodiments the reinforcing members may be partly or wholly offset in an axial direction of the outlet 22. The purpose of the reinforcing members 32 and 34 may be to enable the degree of distension of the opening 26 to be controlled and/or to provide a seal when the outlet 22 is rolled or folded up. The reinforcing members 32 and 34 may bias the opening 26 naturally towards an at least partly closed, or at least partly constricted condition. At least one of the reinforcing members 32 and 34 may have a generally planar natural shape. Additionally, or alternatively, at least one of the reinforcing members 32 and 34 may have a slightly curved or bowed natural shape. A curved shape may result, for example, from storage of the reinforcing members 32 and 34 as roll stock prior to assembly of the pouch 10. A curved natural shape may act to bias the reinforcing members 32 and 34 slightly apart to a partly open condition (although preferably not fully distended). In either case, as described in detail below, by applying pressure to the opposite edges of the outlet 22, the reinforcing members 32 and 34 can be deformed to distend the opening 26.

The first and second reinforcing members 32 and 34 are generally more rigid than the material of the pouch walls 12 and 14. The members 32 and 34 may be capable of being flexed to distend the opening. The reinforcing members 32 and 34 may be resilient. Suitable materials for the reinforcing members 32 and 34 include, for example, styrene, card, plastics coated card, EVA, and polyethylene. The reinforcing members 32 and 34 may be of the same material or of different materials. The reinforcing members 32 and 34 may have substantially the same thickness or different thicknesses. The reinforcing members 32 and 34 may have substantially the same stiffness or different stiffnesses. The reinforcing members 32 and 34 may have substantially the same resilience or different resiliences. The reinforcing members 34 and 32 may be attached to the front and rear walls 12 and 14, respectively, by any suitable method, for example, by adhesive or by welding. In the illustrated embodiment, the reinforcing members 34 and 32 are secured to the exterior faces of the front and rear walls 12 and 14. However, one or both of the reinforcing members 32 and 34 may be attached instead to the interior faces if desired, or embedded within the material of the walls 12 and 14.

In FIG. 4 (and also in FIGS. 7 and 8 referred to later), diagonal hatch lines in one direction represent an area of one reinforcing member, and diagonal hatch lines in the opposite direction represent an area of the other reinforcing member. The region of overlap is represented by the diagonal hatched lines crossing each other.

As best seen in FIG. 4, one of the reinforcing members (the first member 32) may transversely overlie the entire width of a drain passage 36 formed internally in the outlet 22 between the peripheral welds 16 at either lateral edge of the outlet 22. The lateral edges 38 of the first reinforcing member 32 may at least partly overlap the peripheral welds 16. In the illustrated embodiment, the first reinforcing member 32 is shaped to match the width of the outlet 22. In contrast, the second reinforcing member 34 may be shorter than the first reinforcing member 32, and does not overlie the entire width of the internal drain passage 36. Instead, the lateral edges 40 of the second reinforcing member 34 may be slightly inboard of the peripheral welds 16, and may be offset laterally from the corresponding edges 38 of the first reinforcing member 32. The extent of each offset may be of the order of 1-15 mm or more; in this example, 1-9 mm. The extent of the offset may be substantially the same at either edge of the outlet 22, or the extent of the offset may be different at either edge of the outlet 22.

Figure 5:
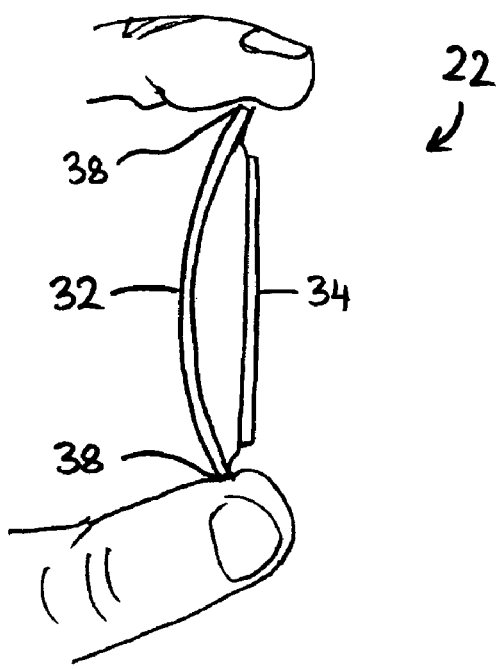
FIG. 5 is a schematic end view of the pouch outlet showing the reinforcing members when pressure is initially applied to begin distending the outlet.
Figure 6:
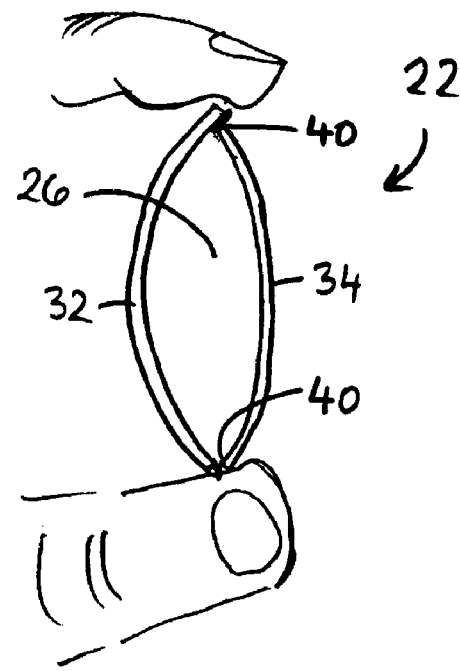
FIG. 6 is a schematic end view similar to FIG. 5, but showing near full distention of the outlet.

It has been found that the offset edges 38 and 40 surprisingly promote the reinforcing members 32 and 34 to bend outwardly in opposite directions when the outlet 22 is squeezed by its edges, even though each reinforcing member may not be configured or creased to promote preferential bending in a certain direction. A slight natural curvature of one or both reinforcing members 32 and 34 may also promote directional bending. Referring to FIG. 5, when a user begins to squeeze the outlet 22 by its edges, the lateral edges 38 of the first reinforcing member 32 are contacted first by the user's fingers to apply pressure to the opposite ends of the first reinforcing member 32 before any pressure is applied to the second reinforcing member 34. This causes the first reinforcing member 32 to bend away from the second reinforcing member 34. The unbent second reinforcing member 34 may naturally obstruct any bending of the first reinforcing member 32 towards the second reinforcing member 34. Referring to FIG. 6, further squeezing of the edges of the outlet 22 then causes the lateral edges 40 of the second reinforcing member 34 either to bear against the user's finger(s) as illustrated at the bottom of FIG. 6, or to bear indirectly against the first reinforcing member 32 as illustrated at the top of FIG. 6, causing the outlet opening 26 to be distended. It can be seen that the different lengths of the first and second reinforcing members 32 and 34 result in the front and rear walls 32 and 34 adopting curvatures with different radii from each other.

Figure 15:
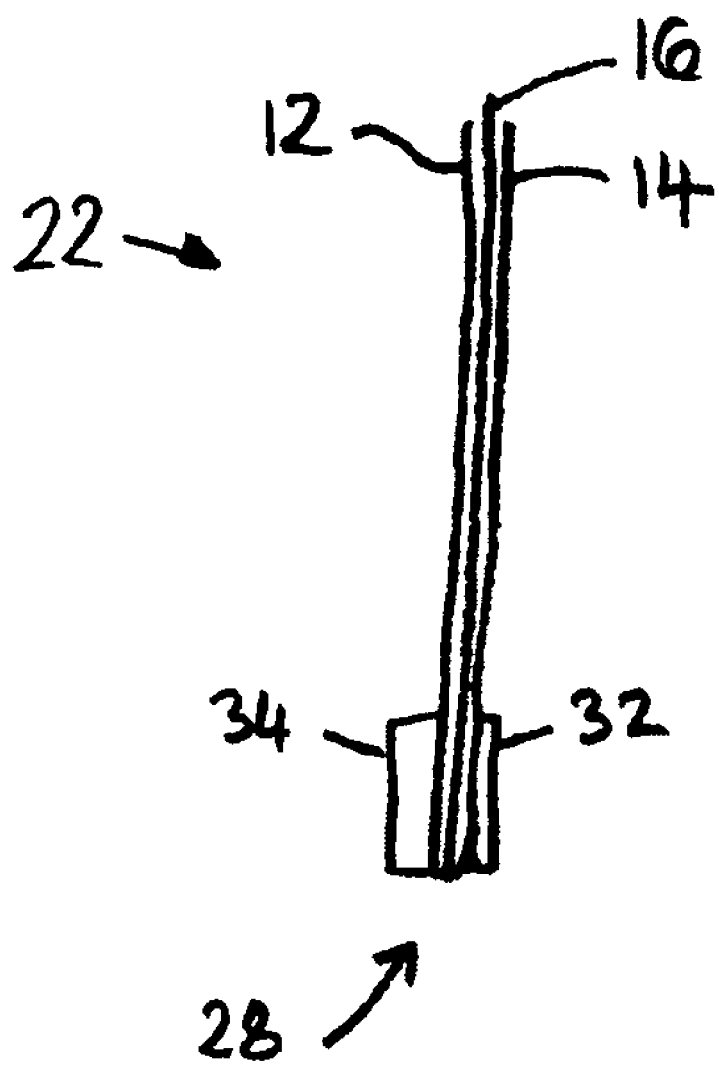
FIG. 15 is a schematic edge view showing an alternative configuration of the reinforcing members.

As mentioned above, the above configuration of the reinforcing members 32 and 34 may provide consistent bending of the reinforcing members 32 and 34 in opposite directions to distend the opening 26, even if the interior surfaces of the pouch walls 12 and 14 may be soiled with sticky faecal matter or fluid. Other configurations of the reinforcing members 32 and 34 may also be used to produce a similar effect. For example, different radii curvatures may be produced by other means and/or the members 32 and 34 may be of different materials and/or may have different resiliences and/or different stiffnesses. One or both of the reinforcing members 32 and 34 may additionally or alternatively have a slight natural curvature. Additionally, or alternatively, the reinforcing members 32 and 34 may be of different thicknesses, as illustrated for example in FIG. 15. In these other configurations, one or more lateral edges 38, 40 of the reinforcing members 32 and 34 may be offset as described earlier, or they may be generally in register.

When the external pressure is released from the edges of the outlet 22, the first and second reinforcing members 32 and 34 tend to return towards their normal configuration, to close or at least narrow the opening 26. Although in the above embodiment, the first reinforcing member 32 is longer than the second reinforcing member 34, it will be appreciated that the lengths of the two members 32 and 34 may be interchanged if desired (for example, the reinforcing members 32 and 34 may be swapped to be on the opposite walls of the pouch 10 to that indicated in the drawings).

Figure 7:
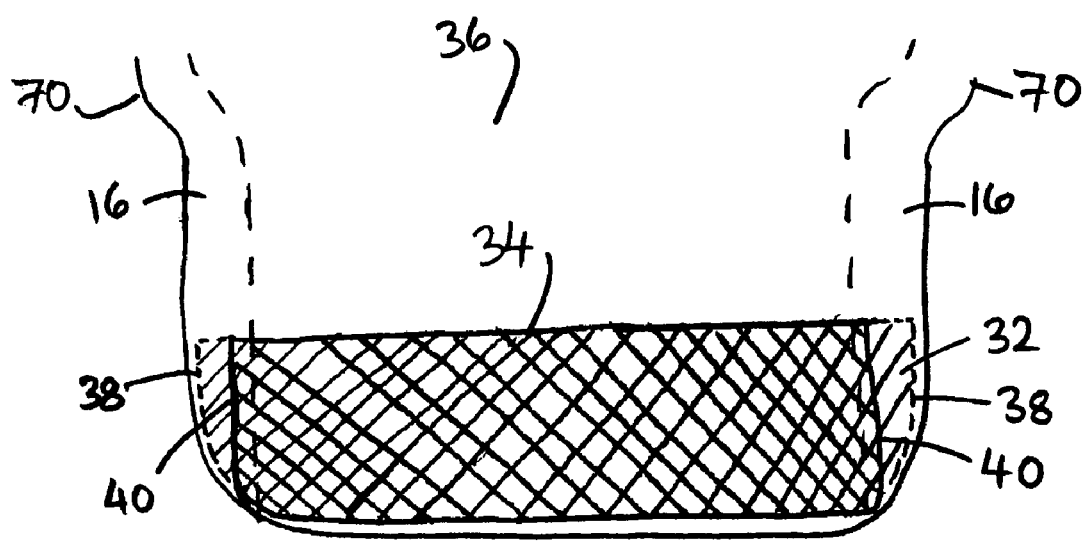
FIG. 7 is a schematic view similar to FIG. 4, but showing an alternative arrangement of reinforcing members.
Figure 8:
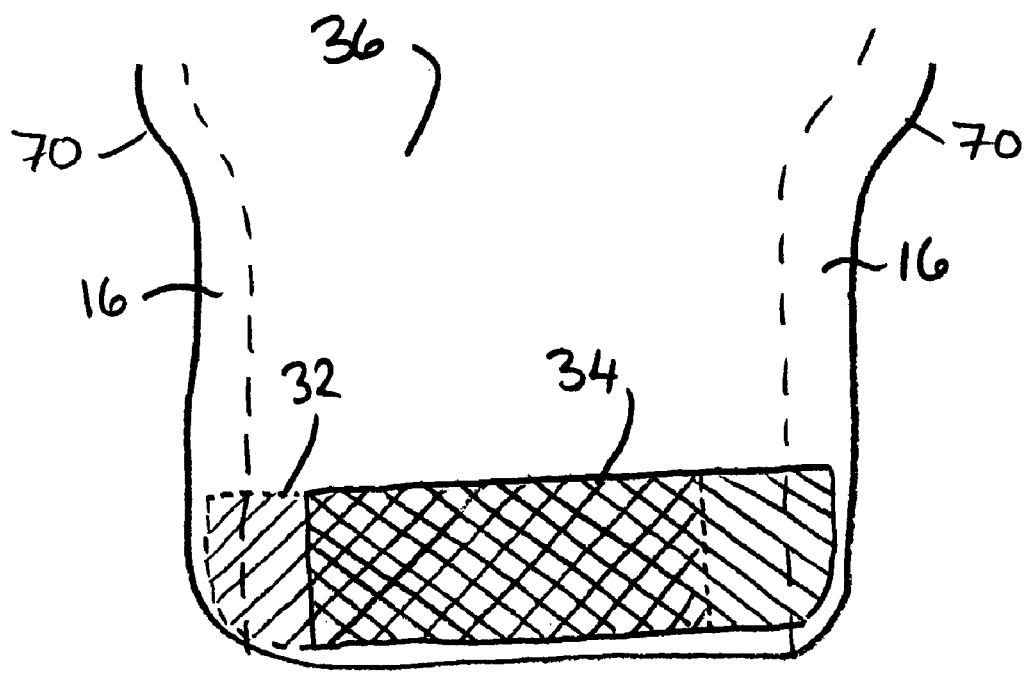
FIG. 8 is a schematic view similar to FIG. 4, but showing a further alternative arrangement of reinforcing members.

FIGS. 7 and 8 illustrate alternative layouts for the first and second reinforcing members 32 and 34 which produce similar effects to promote bending in opposite directions which may principally be as a result of the layout. In FIG. 7, the second reinforcing member 34 is again shorter than the first reinforcing member 32, but is sufficiently long to overlie the entire width of the drain passage 36. The extent of the offset between the edges 38 and the edges 40 is slightly smaller than in the first embodiment. In FIG. 8, the first and second reinforcing members 32 and 34 are of substantially the same length, but are offset laterally to only partly overlap each other. Each reinforcing member is offset laterally with respect to an axis of centreline of the outlet 22 and/or the drain passage 36. The first reinforcing member 32 optionally overlaps one of the peripheral welds 16, and the second reinforcing member 34 optionally overlaps the other of the peripheral welds 16. Optionally, the first and second reinforcing members 32 and 34 may provide reinforcement across the entire width of the drainage passage 36, either individually or together in combination.

A feature of certain of the above designs to promote bending of the reinforcing members 32 and 34 in opposite directions may be that at least one (lateral) edge 38 of the first reinforcing member 32 be offset laterally with respect to a corresponding (lateral) edge 40 of the second reinforcing member. Optionally, another feature of certain of the designs useful for sealing purposes may be that the first and second sealing members together provide reinforcement across the entire width of the drain passage 36 in the outlet 22. It may optional that at least one reinforcing member overlie the entire width of the drain passage 36. Another feature of certain of the above designs useful for sealing purposes may be that both reinforcing members 32 and 34 have smooth surfaces without preformed discontinuities, such as preformed creases. Another feature of certain of the above designs useful for sealing purposes may be that generally transversely extending edges of the reinforcing members 32 and 34 (at least in portions overlapping the drain passage 36) may be generally straight and parallel without any discontinuities.

Referring to FIGS. 1 and 2, the reinforcing members 32 and 34 may be of approximately equal height, and define a unit fold length (indicated in phantom by intervals 42) by which the outlet 22 is folded to bring the outlet to a closed or stowed condition. The reinforcing members 32 and 34 may provide a folding guide so that the outlet 22 may be folded in a consistent manner as intended by the design of the pouch, and such that the fasteners (described below) are presented at least approximately in register. Referring to FIGS. 9(a)-(e), in order to seal the outlet closed, the user folds the outlet 22 from its distal end 28 towards a proximal end 44 (e.g., towards a main collection area of the pouch 10). In the present embodiment, the outlet 22 is configured to be folded up against the front wall 12 of the pouch 14, although in other embodiments, the outlet may be configured to be folded up against the rear wall 14 if desired. Also, in the preferred embodiment, there are four fold stages to bring the outlet 22 to its closed condition, illustrated in FIG. 9(e). However, it will be appreciated that the number of fold stages may be more than four or less than four, if desired. Such folding of the outlet 22 seals the drain 36 in the outlet by tightly wrapping the material of the pouch walls 12 and 14 around the reinforcing members 32 and 34. Such folding may tend to press and/or flatten the reinforcing members 32 and 34 against each other. It will be appreciated that FIGS. 9(a)-(f) are merely schematic, as it is not possible to depict tight folds clearly in the drawings (particularly for FIGS. 9(e) and 9(f)).

An outlet fastener 46 is formed by a first fastener part 46a carried on the front wall 12 of the pouch 10, and by a second fastener part 46b carried on the rear wall 14. The first and second fastener parts 46a and 46b are carried at respective positions on the front and rear walls 12 and 14 such that, when the outlet reaches its closed condition (FIG. 9(e)), the two fastener parts 46a and 46b are substantially in register to contact each other, and can be pressed together to fasten the outlet 22 in its closed condition. The outlet fastener 46 is preferably a distributed mechanical engagement fastener, as described below in more detail.

Figure 9D:
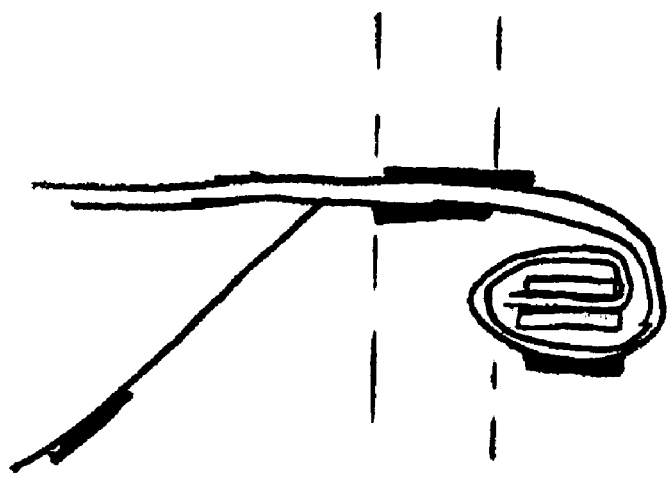
Figure 9C:
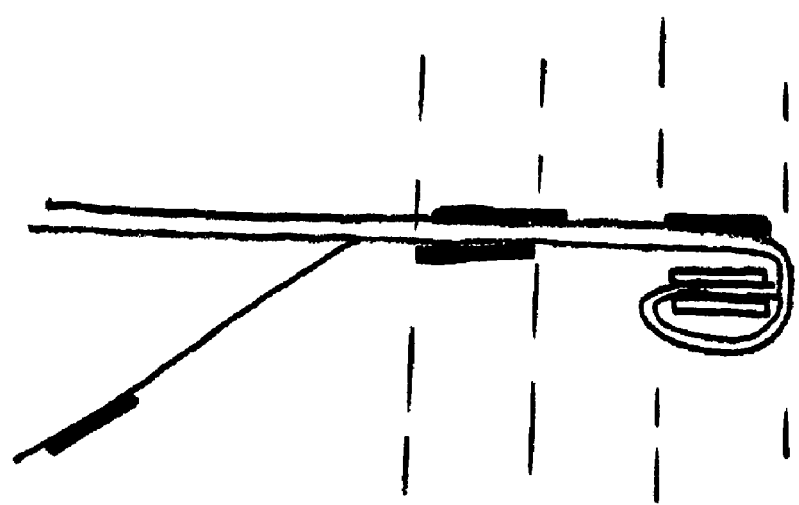
Figure 9F:
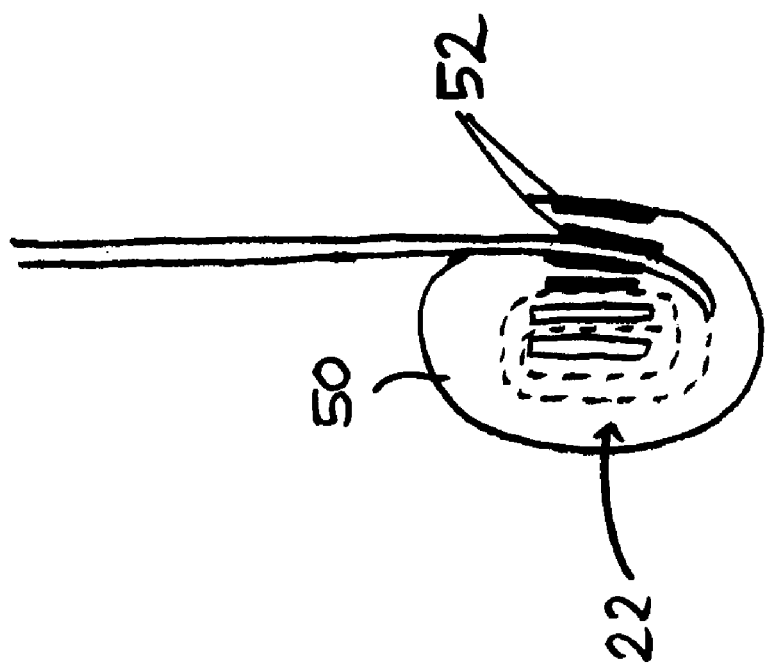
Figure 9E:
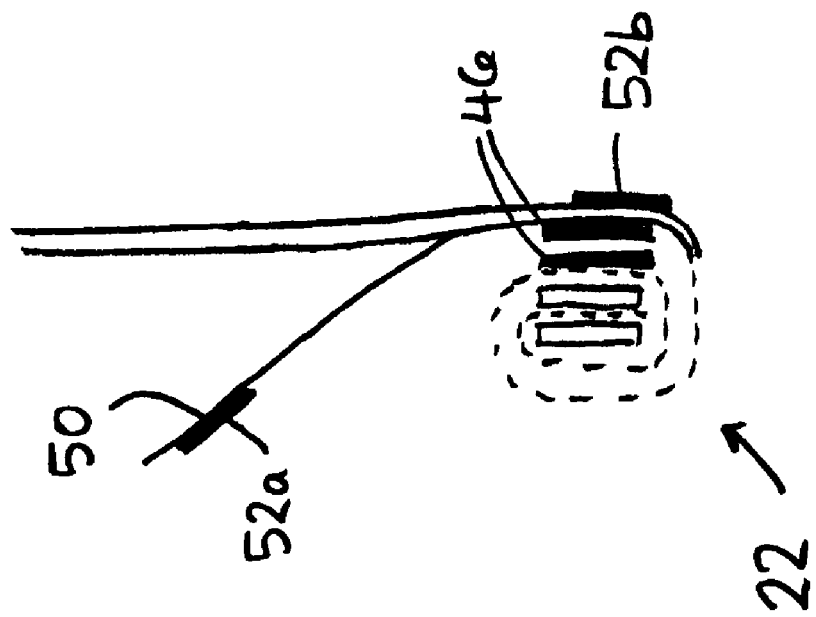

A security flap 50 may be provided on the front wall 12 of the pouch 10. The security flap 50 may be fastened to the front wall 12, for example by welding or by adhesive, or it may be an extension of a layer or portion forming the front wall 12. An attachment weld or adhesive bond may be formed between the flap 50 and the pouch wall either with the flap 50 in a folded up condition, or in a folded down condition. Referring to FIG. 9(f), the security flap 50 is configured to be folded under the outlet 22 when the outlet is in its closed condition, and fastened to the rear wall 14 of the pouch 14. A flap fastener 52 is formed by a first fastener part 52a carried on the security flap 50 and a second fastener part 52b carried on the rear wall 14. The second flap fastener part 52b on the rear wall 14 may be approximately in register with the first outlet fastener part 46a on the front wall 12. The security flap 50 provides a protective sling under the outlet 22 and may provide a measure of additional security. The security flap 50 may prevent the outlet fastener 46 from accidentally becoming unfastened. The security flap 50 may also prevent the outlet 22 from dropping down to its draining position while the security flap 50 is in its fastened condition.

The pouch 10 therefore includes a outlet closure system which is unfastened in two distinct stages. A two-stage approach may provide the user with advantages in terms of controllability of the outlet when it is desired to unfold the outlet 22 from its closed condition. A first stage is to unfasten the flap fastener 52 to release the security flap 50 from around the folded outlet 22. Even with the security flap 50 released, the outlet 22 will not drop down to its unsealed position, because the outlet 22 is itself retained in its closed condition by the outlet fastener 46. A second stage is to unfasten the outlet fastener 46, to release the outlet 22, and to allow the outlet 22 to be unfolded to its extended condition (FIG. 9(a)).

In the extended condition, the user can apply finger pressure to the outlet edges 22, to deform the reinforcing members 32 and 34 to distend the opening 26. The rate at which the pouch contents are discharged through the outlet 22 may be controlled at least partly by varying the distention of the opening 26 according to the amount of finger pressure applied between the outlet edges. At any time, either during emptying, or during initial unfolding and positioning of the outlet 22, the user may substantially stop or prevent any contents from draining through the outlet 22, by pressing and holding the reinforcing members 32 and 34 against each other. This may provide a sufficient seal to temporarily close the outlet 22 even to liquids.

In the illustrated embodiment, the security flap 50 is carried on one face to indicate that the outlet 22 should be folded to its closed condition on that wall of the pouch 10, namely the front wall 12 in the illustrated embodiment. However, it will be appreciated that, if desired, the security flap 50 may be carried on an opposite face to that on which the outlet 22 is intended to be folded to its closed condition.

Figure 10:
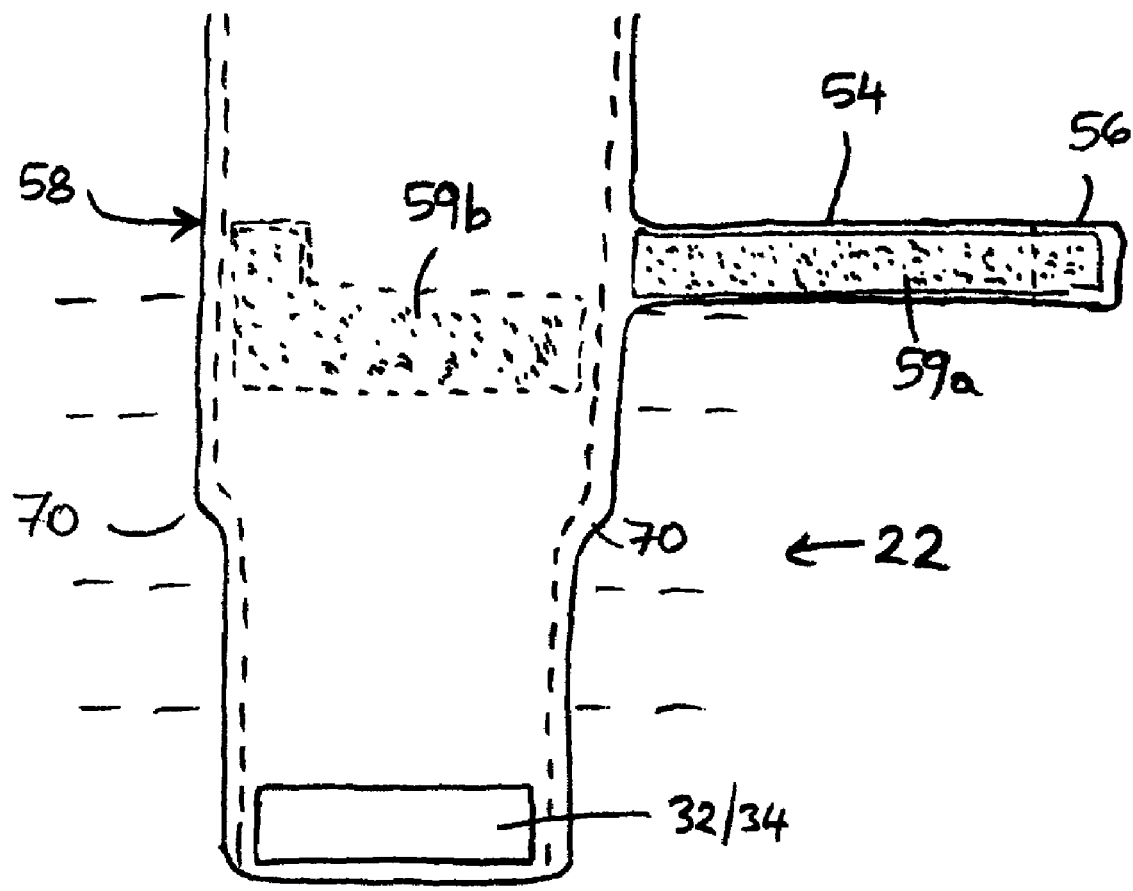
FIG. 10 is a schematic view of the outlet showing an alternative embodiment of a security flap.

FIG. 10 illustrates an alternative design of security flap 54. In FIG. 10, the security flap 54 is configured to be folded laterally around the outlet 22 when the outlet is in its closed condition. The security flap 54 is formed as a lateral extension arm extending from the pouch walls 12 and 14. The security flap is dimensioned to be folded around one face (either the front or rear wall 12 or 14), and a distal portion 56 then folded around the opposite edge 58 to the other face. Inter-engageable flap fastener parts 59a and 59b are carried on the flap 54 and on suitable surfaces of the outlet, such that the fastener part 59b is located at a suitable position for engagement by the flap 54 once the outlet 22 has been folded to its closed condition.

The fasteners 46 and 52 may be any suitable adhesive or mechanical fastener type. The fasteners 46 and 52 may be of the same type of different types. For example, one or both of the fasteners 46 and 52 may be of resealable adhesive type. One or both of the fasteners 46 and 52 may be of a peelable distributed mechanical engagement fastener, in which the fastener parts interlock when fastened together. For example, the fastener parts may be of hook and loop material. The loop material may be a fabric. Additionally or alternatively, one or both of the fasteners 46 and 52 may be of type in which both of the fastener parts 46a/46b or 52a/52b are plastics extrusions. Compared to a fabric fastener part, plastics extrusions may be less vulnerable to soiling. A plastic extrusion may also be less likely to absorb liquids, and may therefore be easier to clean, for example by wiping clean. A plastics extrusion may also be easier to dry after cleaning. Hygiene is of the utmost importance for an ostomate. The ability to clean, or keep clean, a fastener part is extremely advantageous, and plays an important part in customer acceptance of a particular pouch. In particular, it is desirable for the ostomate to be able to immerse the outlet 22 in water to clean the outlet thoroughly, and to dry the surfaces before reusing the pouch.

One or both of the fasteners 46 and 52 may also be of a positive snap-engagement type, so that the user can positively detect when the fastener parts fasten together. This is especially advantageous for a user who's vision might be impaired, and who might find it difficult to verify visually that the fastener is correctly fastened.

Figure 11:
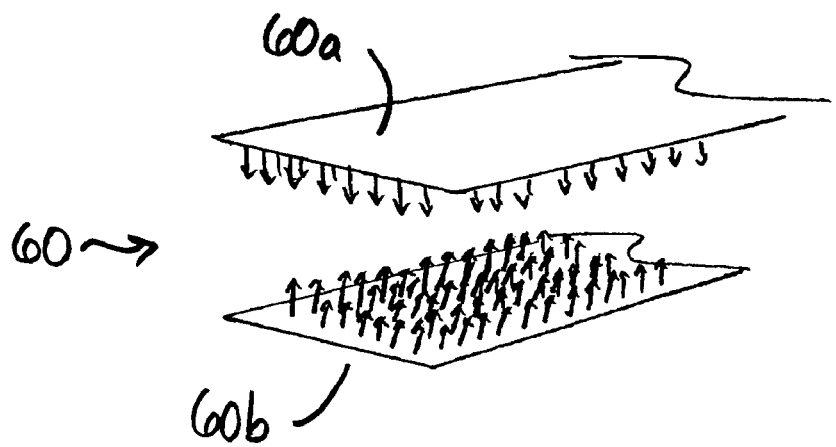
FIG. 11 is a schematic perspective view showing a hook-hook fastener in isolation.
Figure 12:
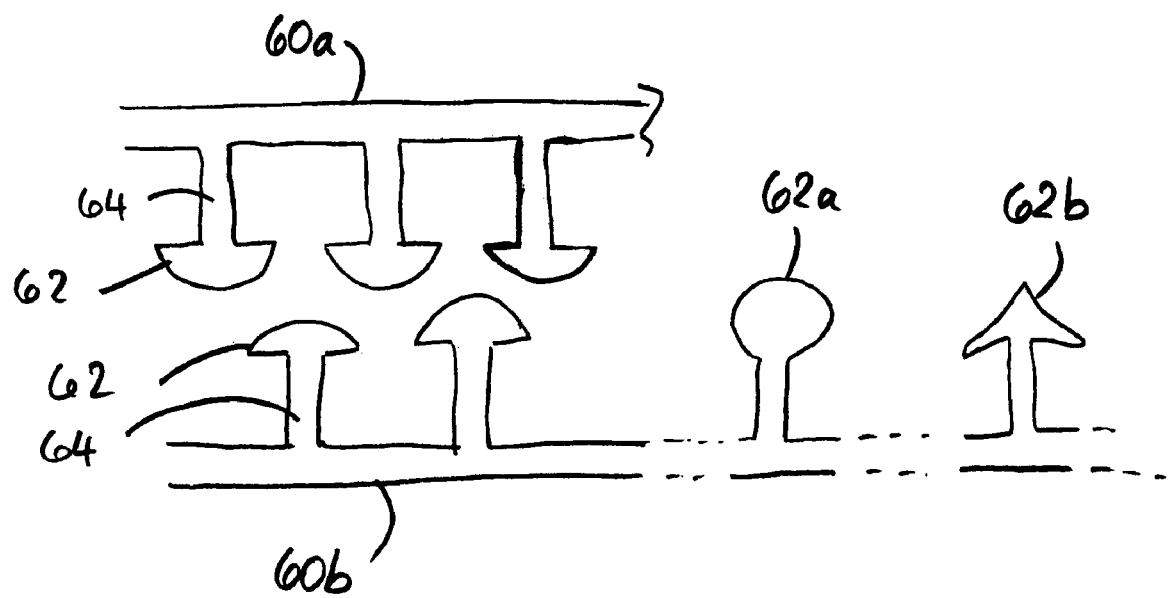
FIG. 12 is a schematic cross section showing profiles of hook-hook fastener parts.

Referring to FIGS. 11 and 12, an especially advantageous form of fastener 46 or 52 is distributed mechanical fastening hook-hook type fastener 60, in which interlocking mechanical engagement may be generally distributed over a two-dimensional area of the fastener. The fastener parts may be peelable apart, for example by progressive peeling from an edge. Each fastener part 60a and 60b comprises a plurality of projections 62 on stalks 64. The projections 62 may be undercut. For example, the projections 62 may extend on either side of the stalk 64 and define a flat mushroom-headed profile. The stalks may be arranged in a regular array of rows and/or columns. When the two fastener parts 60a and 60b are pressed together, the opposing stalks 64 interdigitate, such that the projections 62 on one part 60a interlock with the projections 62 of the other part 60b. FIG. 12 also shows examples of other possible shapes of the projections 62, in the form of a bulbous head 62a, and in the form of a barb or arrowhead 62b.

Each fastener part 60a, 60b may be a plastics extrusion. The projections 62 may interlock with a positive, detectable snap engagement. The two parts 60a and 60b may be substantially the same as each other, or the two parts 60a and 60b may be of different forms. A benefit of the two parts 60a and 60b being the same is that this can simplify manufacturing of the pouch, and it also increases the flexibility of design for pouch designers.

A suitable hook-hook fastener is, for example, the "Easy Lock" fastener produced by Aplix.

Figure 13:
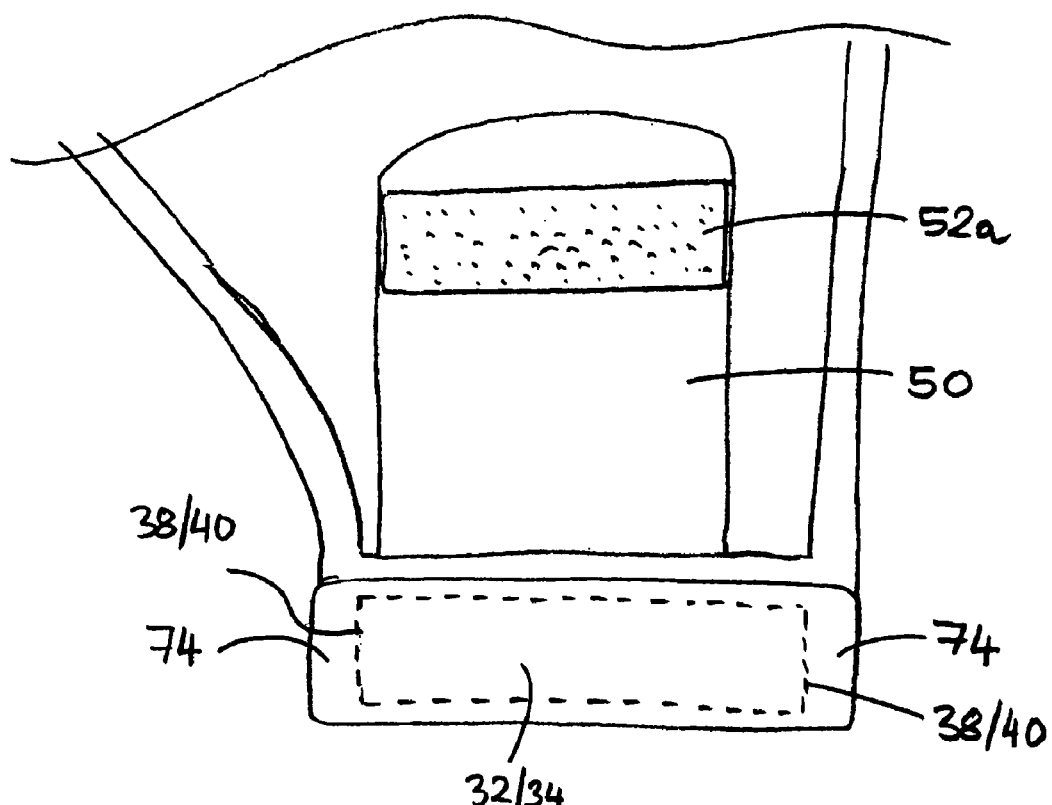
FIG. 13 is a schematic front view showing a detail of the front of the pouch when the outlet is in its closed condition.

As can be seen in FIGS. 1, 2, 4, 7 and 8, the external profile of the outlet may include a lateral step 70 partway between the proximal end 44 of the outlet 22, and the location of the reinforcing members 32 and 34. The lateral step 70 may be of the order of about 1 to 5 mm, or more, at each side edge of the outlet 22. Referring to FIG. 13, when the outlet 22 is folded to its closed condition, the peripheral portions 72 above the step 70 provide generally soft deformable cushion zones 74, which overlie the relatively abrupt edges 38 and 40 of one or both of the reinforcing members 32 and 34. This can make the pouch more comfortable to wear, and may avoid the edges 38 and 40 of one or both of the reinforcing members 32 and 34 from catching on the wearer's skin or clothes.

Figure 14:
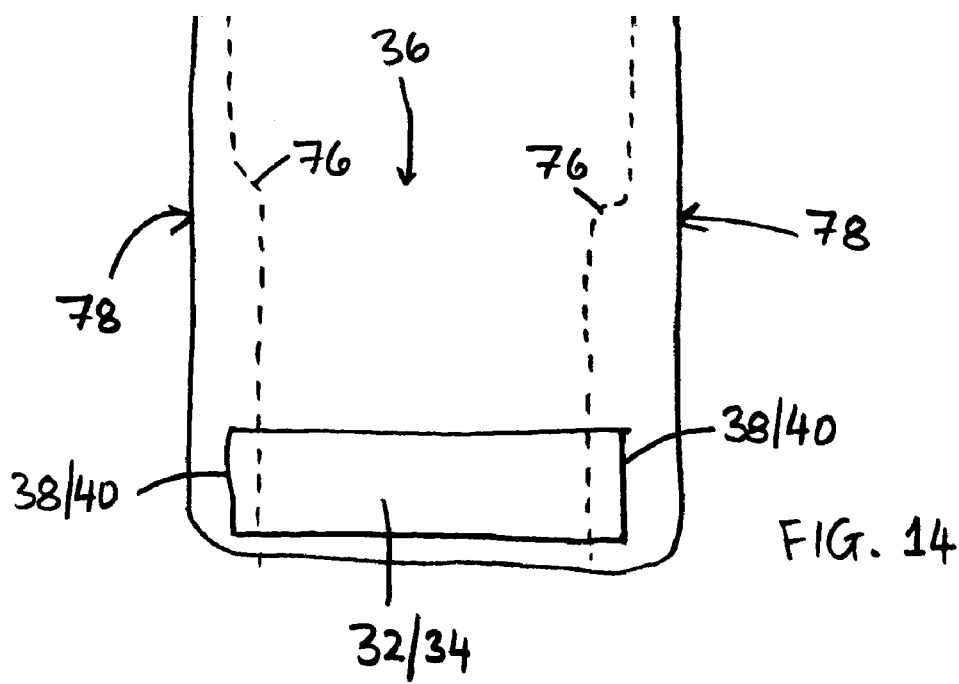
FIG. 14 is a schematic front view showing an alternative configuration of a step in the profile of the outlet.

Referring to FIG. 14, an alternative technique for implementing the same principle is to provide an internal profile step 76 in the shape of the passage 36 within the outlet 22. The internal step 76 ensures that peripheral portions 78 of the outlet 22 provide a generally soft deformable cushion outside over the edges 38 and 40 of one or both of the reinforcing members 32 and 34. It will be appreciated that a feature of the profile step, whether an external step 70, or an internal step 74, is to provide sufficient pouch wall material extending laterally beyond the abrupt edges 38 and 40 of the reinforcing members to obtain a cushioning effect.

Figure 16:
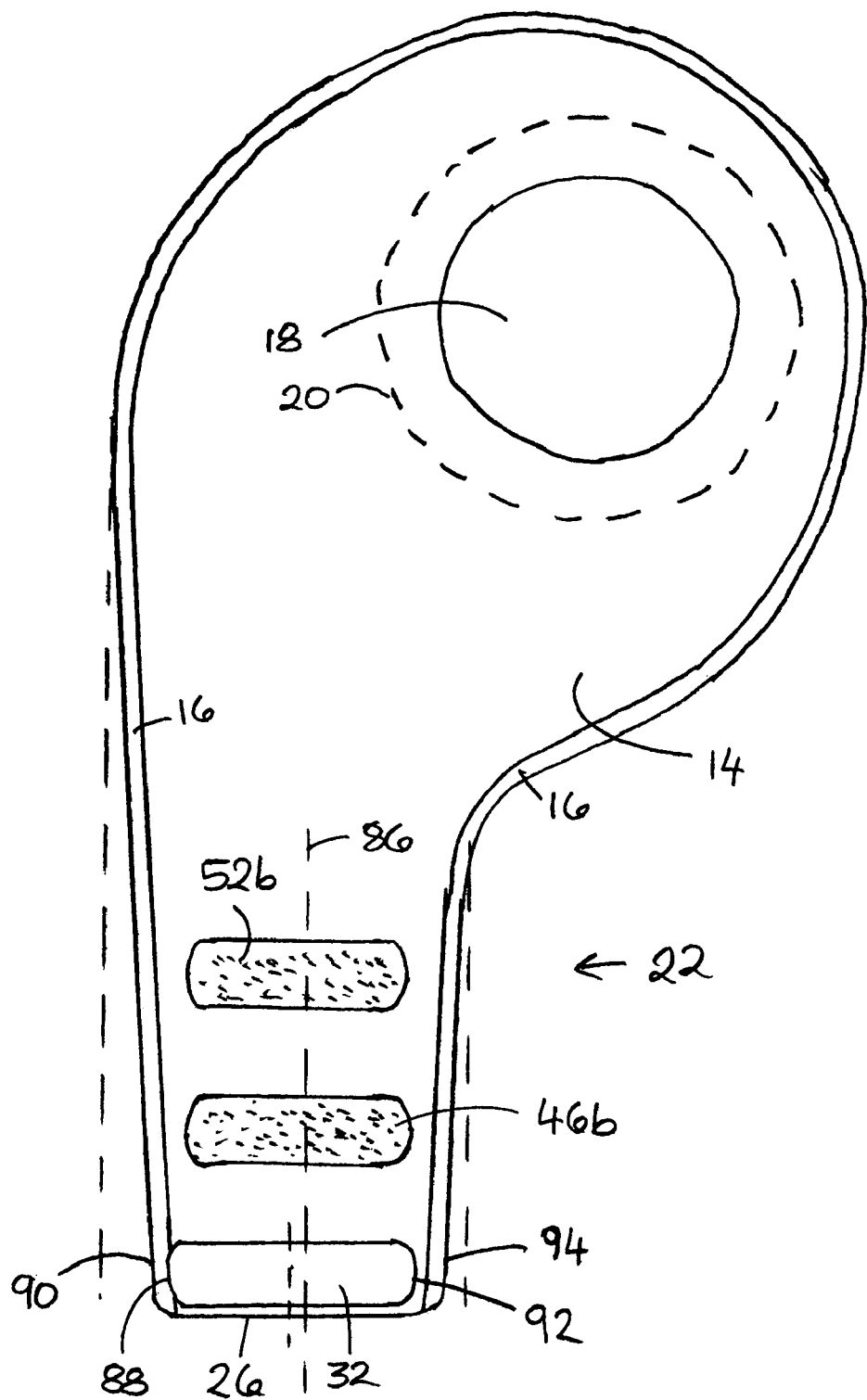
FIGS. 16 and 17 are schematic front/rear views showing a further alternative arrangement of the outlet and reinforcing members.
Figure 17:
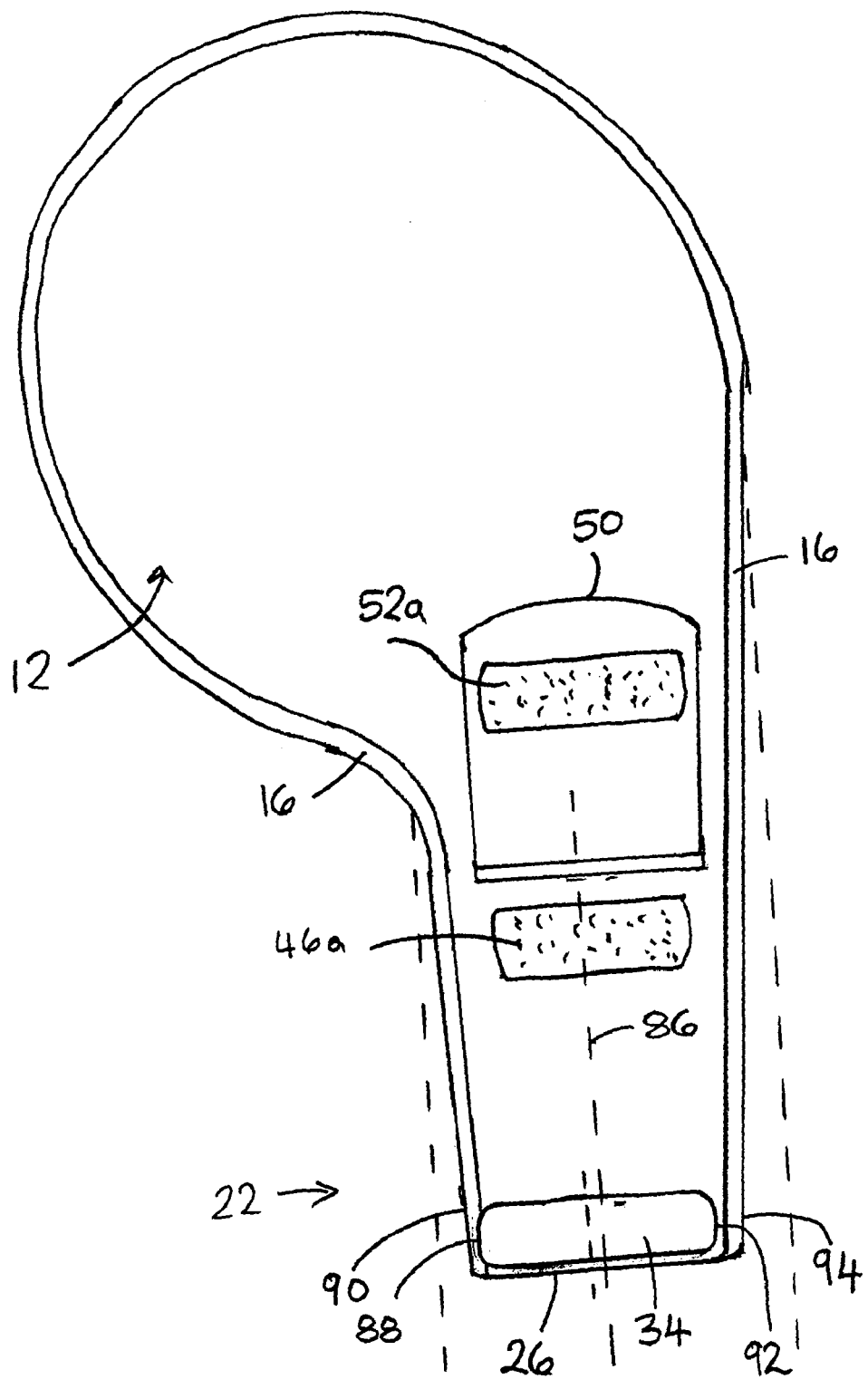

Referring to FIGS. 16 and 17, a yet further alternative for implementing a similar principle may be for the outlet 22 to taper in width, such that the outlet 22 narrows towards the opening 26. The taper may extend over a majority of the length of the outlet 22 between a proximal end 80 and the opening 26 at the distal end 82. The taper may provide the same effect as that described above, for providing a cushion zone 84 of soft pouch material laterally outside the edges of the reinforcing members 32 and 34 when the outlet 22 is folded up. A tapered shape may be additionally advantageous in reducing any risk of faecal matter being trapped at an abrupt step. In a similar manner to that described for the lateral step, the tapered shape may also be formed internally, for example, by an internal weld, such that the drain passage 36 may taper in width towards the opening 26.

In FIGS. 16 and 17, the arrangement of the reinforcing members 32 and 34 may be similar to that illustrated in FIG. 8. The reinforcing members 32 and 34 may be of about the same length as each other. Each reinforcing member 32, 34 may be offset laterally with respect to an axis or centreline 86 of the outlet 22 and/or the drain passage 36. The reinforcing members 32 and 34 may offset laterally with respect to each other. A first edge 88 of at least one (or each) reinforcing member may be offset laterally from an adjacent edge 90 of the outlet 22 to provide a cushion zone similar to that described above. The amount of the cushion offset may, for example, be between 0 mm (no offset) and 5 mm or more, more preferably between 0 and 3 mm inclusive. Additionally or alternatively, a second edge 92 of at least one (or each) reinforcing member may be offset laterally from an adjacent edge 94 of the outlet to provide a cushion zone. The amount of the cushion offset may, for example, be between 0 mm (no offset) and 12 mm or more, more preferably between 1 and 9 mm inclusive. The edges 88 and 92 of each reinforcing member 32, 34 may be radiused to avoid any sharp corners that might be uncomfortable for the ostomate when the pouch is worn.

In all of the foregoing embodiments, one or more of the fastener parts 46a, 46b, 52a and 52b may be shaped or located such that, when the outlet 22 is folded to its closed condition, the fastener parts 46a, 46b, 52a and 52b lie inboard of peripheral edges of the pouch walls, such that the peripheral regions of the pouch walls may provide soft cushioning zones to cushion the edges of the fastener parts. Especially in the case of fastener parts in the form of plastics extrusions, the fastener parts may be generally stiffer, or more rigid, than the pouch wall material. The soft peripheral zones laterally outside the more rigid fasteners may make the pouch more comfortable to use and to wear.

The above configuration of the fastener parts and/or the reinforcing members with respective cushioning zones, may be referred to as "island" placement, so that one or more lateral edges of the fastener parts and/or reinforcing members are inboard of a cushioning zone of material. Such island placement may be apparent in the unfolded, extended condition of the outlet 22, or may occur only when the outlet 22 is folded to its closed condition.

Figure 18:
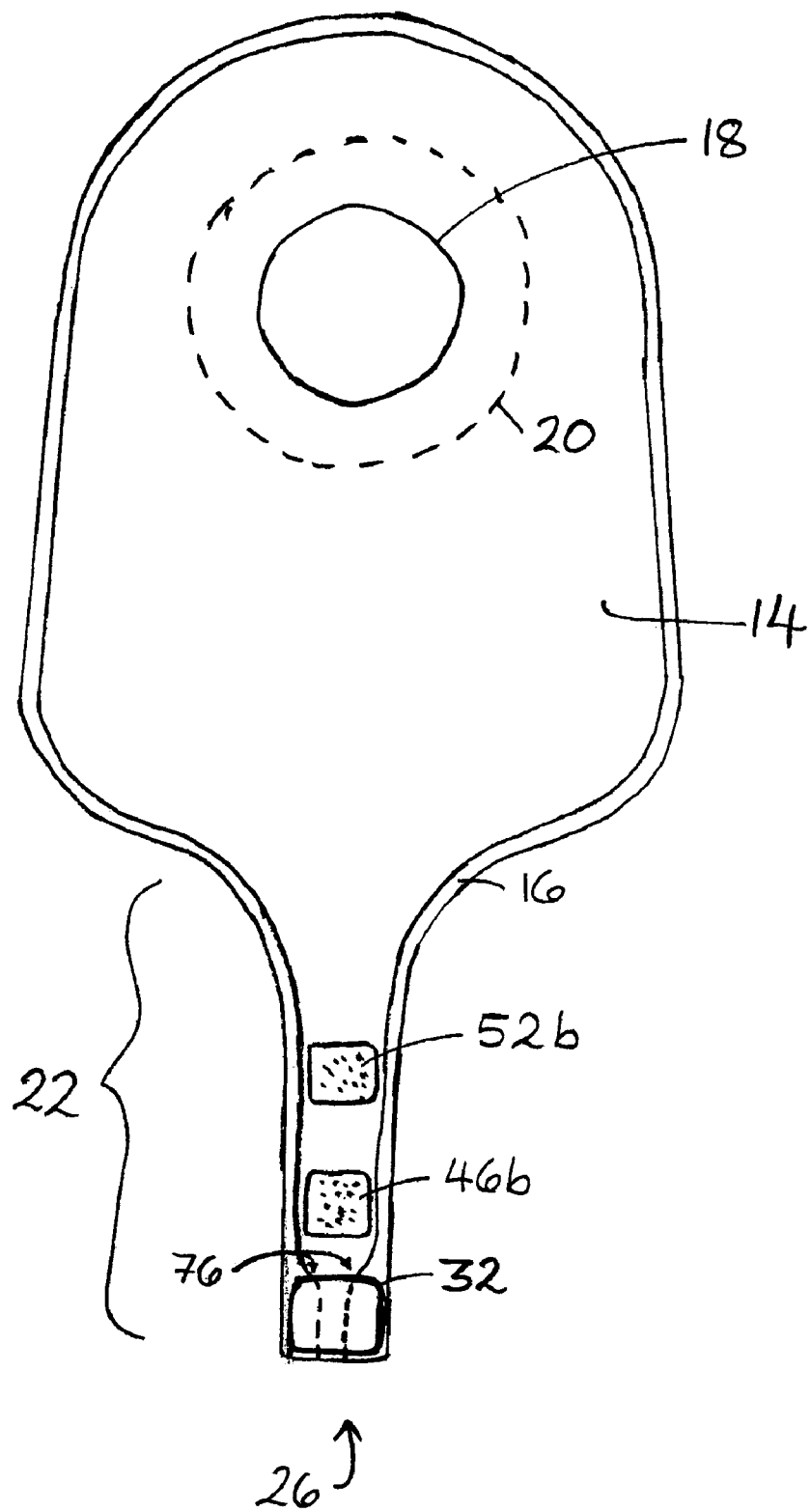
FIG. 18 is a schematic front view showing a further embodiment in the form of a urine pouch.
Figure 19:
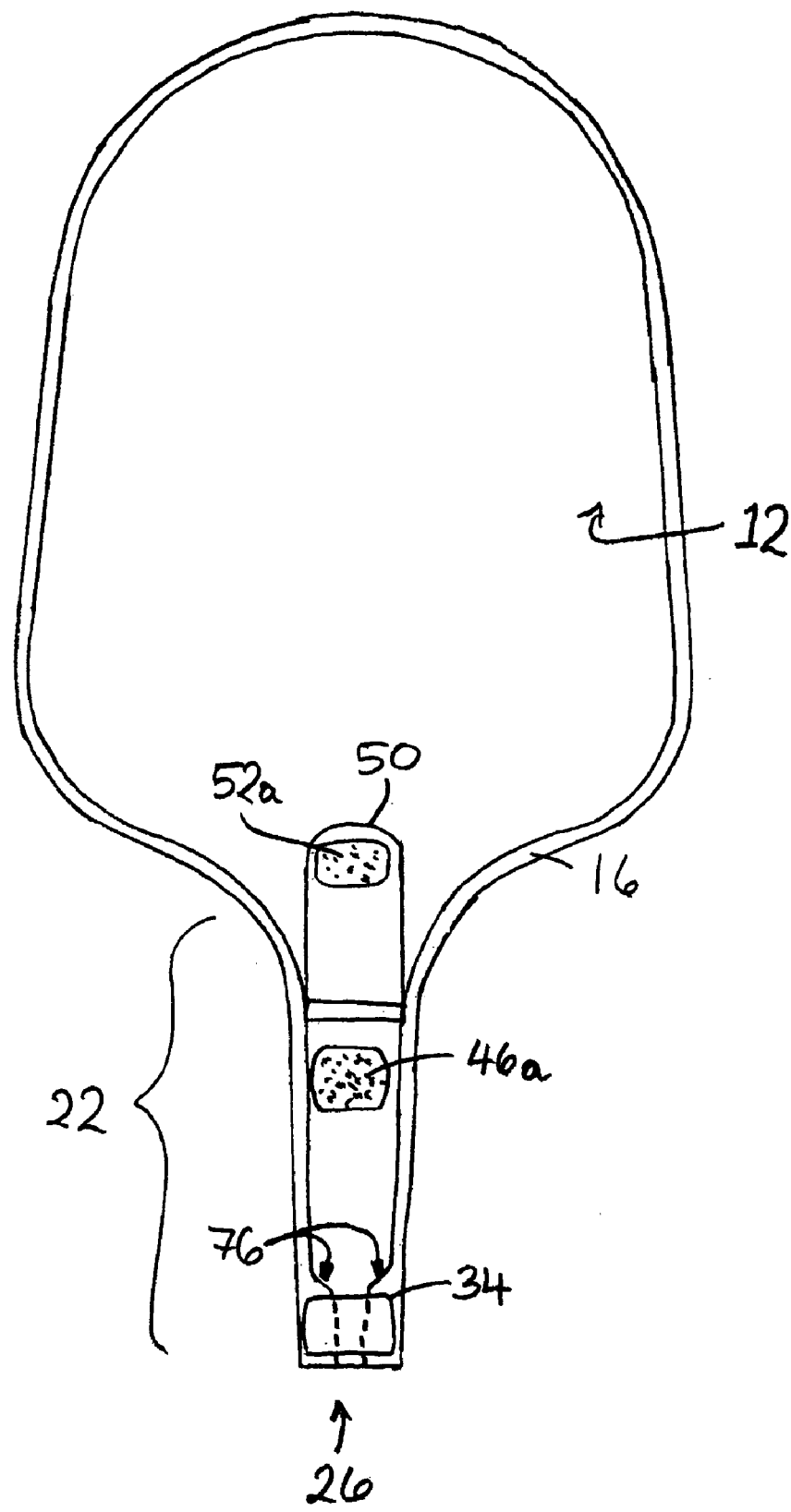
FIG. 19 is a schematic front view showing a yet further embodiment in the form of a urine pouch.
Figure 20:
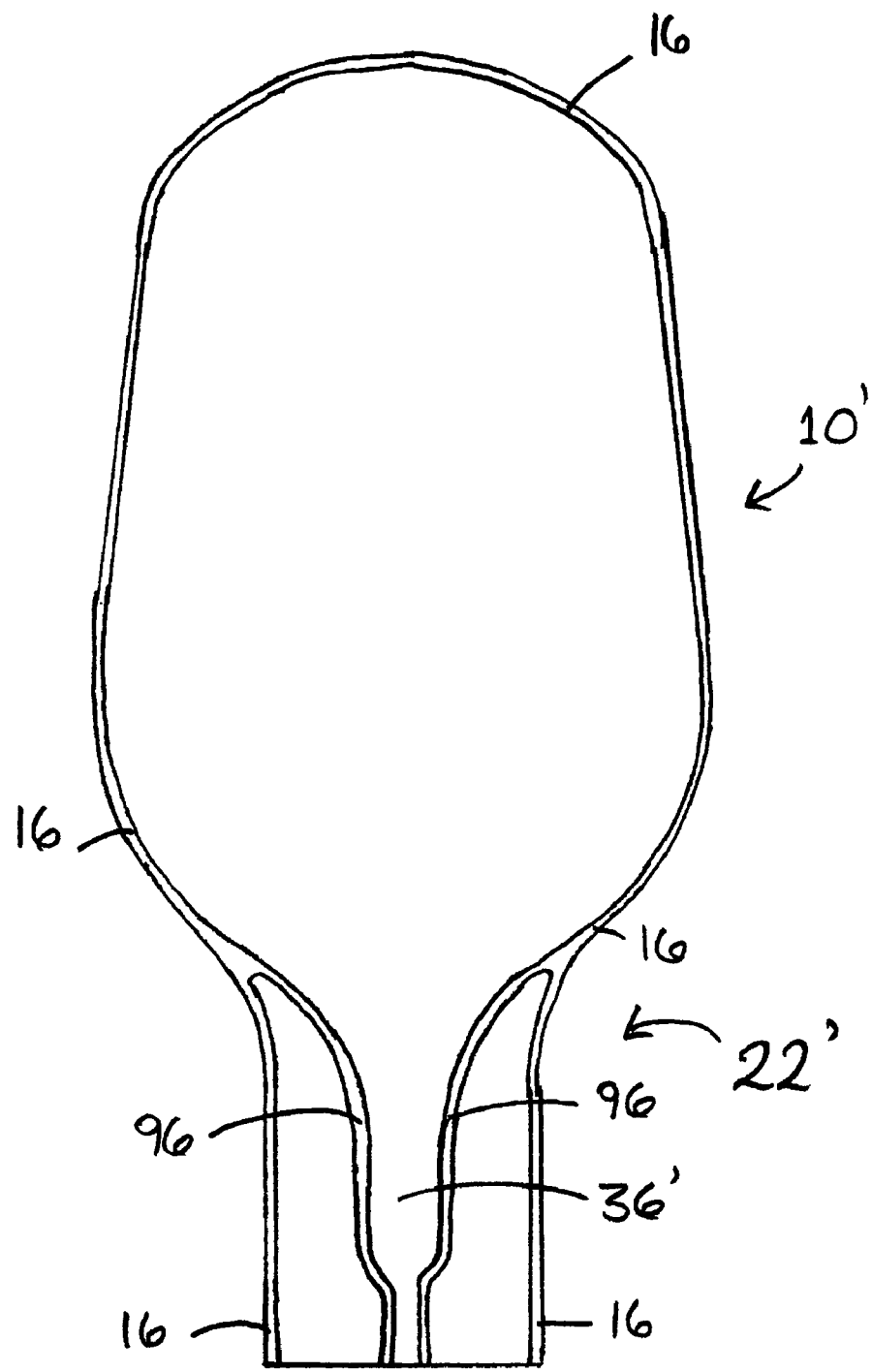
FIG. 20 is a schematic front view showing a yet further embodiment in the form of a urine pouch.

The foregoing embodiments may be especially (although not exclusively) suitable for use as drainable ileostomy pouches. FIGS. 18-20 illustrate further embodiments that may be especially (although not exclusively) suitable for use as drainable urine pouches, for example, urostomy pouches.

In FIGS. 18 and 19, the main difference from the previous embodiments may be that the outlet 22 is narrower than in the previous embodiments. The narrower outlet 22 may be suited for draining predominantly liquid contents from the pouch 10. The pouch 10 may include any or all of the features previously described, but in a form suited to the narrower outlet 22. For example, the pouch may include the reinforcing members 32 and 34, the security flap 50, the fasteners 46 and 52, and/or the entrance aperture 18. The outlet 22 may include the internal profile step 76 in the shape of the drain passage 36, for providing cushion zones laterally outside the reinforcing members 32 and 34. The step 76 may be a tapered step or an abrupt step. The step 76 may be located just above, or near the upper edges of, the reinforcing members 32 and 34, to define a narrow liquid passage at the opening 26. The reinforcing members 32 and 34 may be generally opposed to each other. Optionally, at least one edge of at least one of the reinforcing members 32, 34 may be laterally offset relative to a corresponding edge of the other reinforcing member 32, 34. Alternatively, the reinforcing members 32 and 34 may be substantially in register with each other. Optionally, at least one edge of at least one of the reinforcing members 32, 34 may be offset relative to an outer edge of the outlet 22, to define a cushion zone.

Referring to FIG. 20, a further embodiment may include a hybrid outlet 22'. The hybrid outlet 22' may have an internal narrow drain passage 36' similar to that illustrated in FIGS. 18 and 19. The hybrid outlet 22' may have an external profile similar to the wider outlet of the embodiments of FIGS. 1-17. The narrow drain passage 36' may be defined by one or more lines of attachment 96, for example, weld lines or adhesive bond lines, between the front and rear walls 12 and 14, and intersecting the peripheral weld 16. The lines of attachment 96 may define a tapered and/or stepped shape of drain passage 36'. In FIG. 20, the reinforcing members 32 and 34, the fasteners 46 and 52 and the flap 50 may not be shown, to avoid cluttering the drawing, although it will be appreciated that these elements may be provided in the same manner as in previous embodiments.

It will be appreciated that various modifications may be made within the scope and principles of the invention, and various features described above may be replaced if these feature are not required.

Although the preferred embodiments have been described in the context of an ostomy pouch, it will be appreciated that the same principles may be used with other types of pouches for body waste, for example, hygiene bags and urine bags.

The invention claimed is:

1. A drainable pouch for collecting human waste, the pouch comprising:
   a. opposing pouch walls having an opening therebetween, the pouch walls tapering down to an outlet having an outlet opening;
   b. first and second deformable reinforcing members, each reinforcing member being attached to an opposing pouch wall near or at the outlet opening, the first reinforcing member having two opposite first lateral edges, the second reinforcing member having two opposite second lateral edges, each of the first lateral edges being proximate to a respective second lateral edge, the first and second reinforcing members being deformable by manual application of pressure to opposite lateral edges of the reinforcing members so as to controllably distend the outlet opening; wherein a first lateral edge of the first reinforcing member is offset laterally with respect to a proximate second lateral edge of the second reinforcing member;
   c. the outlet being flexible and foldable from an extended condition to a stowed condition;
   d. a plurality of outlet fasteners on at least one pouch wall capable of separably interlocking for securing the outlet in its stowed condition;
   e. a security flap extending freely from an end secured to a pouch wall, the security flap having a smooth outside surface and an underside surface, the security flap being flexible and foldable over and around the outlet when the outlet is in its stowed condition; and
   f. a flap fastener on the underside of the security flap, the flap fastener being capable of securing the security flap in its folded condition over and around the outlet with the smooth outside surface of the security flap exposed and the outlet stowed and covered.

2. The drainable pouch according to claim 1, wherein the first reinforcing member has a first lateral edge that overlaps and extends beyond a proximate second lateral edge of the second reinforcing member.

3. The drainable pouch according to claim 1, wherein the first and second reinforcing members are of different lengths.

4. The drainable pouch according to claim 1, wherein the first and second reinforcing members are of about the same length, and are partly offset in a lateral direction so as to partly overlap each other.

5. The drainable pouch according to claim 1, wherein the first and second reinforcing members have an overall length that extends substantially entirely across the width of the outlet opening.

6. The drainable pouch according to any claim 1, wherein at least one of the first and second reinforcing members overlies substantially entirely the width of the outlet opening.

7. The drainable pouch according to claim 1, wherein lateral edges at both opposite ends of the reinforcing members are offset laterally from each other.

8. The drainable pouch according to claim 1, wherein the first and second reinforcing members are attached to exterior faces of the pouch.

9. The drainable pouch according to claim 1, wherein the pouch is an ostomy pouch.

10. The drainable pouch according to claim 1, wherein the first and second reinforcing members are of different lengths and have different magnitude radii of curvature.

11. The drainable ostomy pouch according to claim 1, wherein the first and second reinforcing members are composed of different materials.

12. The drainable pouch according to claim 1, wherein the first and second reinforcing members have a different resilience and/or a different stiffness.

13. The drainable pouch according to claim 1, wherein the first and second reinforcing members are of different thicknesses.

14. The drainable pouch according to claim 1, wherein the outlet fasteners include first and second fastener parts that have the same fastener projections as each other.

15. The drainable pouch according to claim 14, wherein the first and second fastener parts provide a snap engagement when the fastener parts are pressed together.

16. The drainable pouch according to claim 14, wherein each of the first and second fastener parts comprises stalks with projections for interlocking with projections of the other fastener part when the two fastener parts are pressed together.

17. The drainable pouch according to claim 14, wherein the first fastener part is carried on a first exterior face of the pouch, and the second fastener part is carried on a second exterior face of the pouch opposite the first face.

18. The drainable pouch according to claim 14, wherein at least one of the fastener parts is on a portion of the outlet for directly securing the outlet in its stowed condition.

19. The drainable pouch according to claim 14, wherein at least one stiffener part is located such that, in the stowed condition of the outlet, a periphery edge of the stiffener part is inboard of a zone of cushioning material.

20. The drainable pouch according to claim 1 wherein the outlet includes a lateral step or taper at a position between a reinforcing member and a proximal end of the outlet, for providing a zone of cushioning material outside an edge of a reinforcing member when the outlet is folded to its stowed condition.

21. The drainable pouch according to claim 20, wherein the reinforcing member overlies at least one boundary of a drain passage in the outlet.

22. The drainable pouch according to claim 20, wherein the lateral step or taper is in the external shape of the outlet.

23. The drainable pouch according to claim 20, wherein the lateral step or taper is in an internal shape of the outlet.

24. The drainable pouch according to claim 20, wherein the taper extends over at least a majority of the length of the outlet.

* * * * *